United States Patent [19]

Jarczyn

[11] Patent Number: 4,538,621
[45] Date of Patent: Sep. 3, 1985

[54] URODYNAMIC CATHETER

[75] Inventor: Henry N. Jarczyn, Ontario, Canada

[73] Assignee: Urotek Inc., Mississauga, Canada

[21] Appl. No.: 460,769

[22] Filed: Jan. 25, 1983

[51] Int. Cl.³ .............................................. A61B 5/00
[52] U.S. Cl. ..................................... 128/748; 604/102
[58] Field of Search ................. 128/748, 774; 604/54, 604/96, 102–103, 97–101

[56] References Cited

U.S. PATENT DOCUMENTS

| 3,394,705 | 7/1968  | Abramson ........................ 604/96 X |
| 3,437,088 | 4/1969  | Bielinski . |
| 3,480,003 | 11/1969 | Crites . |
| 3,483,859 | 12/1969 | Pittman ........................... 604/96 X |
| 3,769,981 | 11/1973 | McWhorter ......................... 604/96 |
| 3,811,450 | 5/1974  | Lord ................................. 604/96 |
| 4,006,735 | 2/1977  | Hittman et al. . |
| 4,023,562 | 5/1977  | Hynecek et al. ................... 128/748 |
| 4,114,625 | 9/1975  | Onat ................................. 604/96 |
| 4,136,681 | 1/1979  | Hon .................................. 128/748 |
| 4,155,364 | 5/1979  | Boxer ............................... 604/54 |
| 4,168,703 | 9/1979  | Kenigsberg ....................... 128/748 |
| 4,191,196 | 3/1980  | Bradley et al. .................... 128/733 |
| 4,211,233 | 7/1980  | Lin .................................. 604/96 X |
| 4,214,593 | 7/1980  | Imbruce et al. ................... 128/748 |
| 4,217,911 | 8/1980  | Layton ............................. 128/748 |
| 4,252,131 | 2/1981  | Hon et al. ......................... 128/748 |
| 4,265,243 | 5/1981  | Taylor .............................. 128/760 X |
| 4,301,811 | 11/1981 | Layton ............................. 128/748 |
| 4,367,740 | 1/1983  | Evanoski .......................... 604/103 X |
| 4,407,301 | 10/1983 | Streisinger ....................... 604/103 X |
| 4,484,585 | 11/1984 | Baier ............................... 128/748 |

OTHER PUBLICATIONS

Glen et al.; "Continuous Flow Cystometry and Urethral Pressure Profile Measurement with Monitored Intravesical Pressure"; Urol. Res. 1, 1973, pp. 97–100.

Primary Examiner—Lee S. Cohen
Assistant Examiner—Angela D. Sykes
Attorney, Agent, or Firm—Sim & McBurney

[57] ABSTRACT

There is provided a urodynamic catheter which includes a tube having at least three lumens, each communicating with openings spaced at different distances from the closed leading end of the tube. In a further embodiment, an additional lumen is provided in the tube, communicating with the interior of a balloon which is attached to the tube and located between the second and third openings, measured away from the leading end.

10 Claims, 4 Drawing Figures

URODYNAMIC CATHETER

This invention relates generally to the medical field of Urodynamic studies, and has to do particularly with the construction of an improved urodynamic catheter adapted to conduct urodynamic tests on the lower urinary tract.

BACKGROUND OF THIS INVENTION

Urodynamic tests are diagnostic procedures, the purpose of which is to assess the physiologic properties of the lower urinary tract, i.e. the bladder and urethra.

The urinary bladder and the urethra work together as a unit to serve the double purpose of collecting and conveying urine. The bladder is composed mostly of small muscles which are to a large degree under voluntary control. Muscle bundles run in different directions and from layer to layer.

The adaptation of the bladder to the changing urine volume is mainly due to the viscal-elastic property of the organ. The bladder wall, in a healthy individual, is able to expand without any significant increase in tension as the bladder fills with urine. One of the major urodynamic tests involves filling the bladder with a saline solution, and simultaneously measuring the intravesical pressure. The plot of pressure against volume of contents during this filling is called a cystometrogram, and the early portion of this graphical representation of pressure against volume is substantially flat in a healthy individual. When the individual is instructed to void, or when the urge to void arises automatically, the pressure inside the bladder increases.

Another standard urodynamic test is called the urethral pressure profile (UPP). This test is typically carried out by inserting a catheter having a side opening and a lumen communicating with that opening. A dilute saline solution is pumped into the lumen and out through the side opening at a fixed rate, while the catheter is steadily withdrawn from the urethra at a substantially constant speed. A plot of the back pressure in the line between the pump and the side opening, against the physical distance of the opening along the urethra, yields the UPP. Typically, as the opening passes a location of constriction, whether normal or abnormal, the back pressure rises, and appears as a spike or hump in the graphical representation of pressure against distance.

Another factor related to the test just mentioned is the functional profile length, which is basically the length of the urethra over which the pressure profile is taken.

One of the important parameters derived from the urethral pressure profile test (UPP) is what is called the maximum urethral closure pressure, which is the difference between the maximum pressure derived by the UPP test and the intravesical pressure of the bladder.

Prior patents of interest to this subject matter are as follows:

U.S. Pat. No. 4,136,681, issued Jan. 30, 1979, to Edward H. Hon

U.S. Pat. No. 168,703, issued Jan. 30, 1979, to Kenneth Kenigsberg

U.S. Pat. No. 4,191,196, issued Mar. 4, 1980, to Bradley et al

U.S. Pat. No. 4,217,911, issued May 5, 1981, to Terry N. Layton

U.S. Pat. No. 4,252,131, issued Feb. 24, 1981, to Hon et al

U.S. Pat. No. 4,006,735, issued Feb. 8, 1977, to Hittman et al

U.S. Pat. No. 4,023,562, issued May 17, 1977, to Hynecek et al

U.S. Pat. No. 3,480,003, issued Nov. 25, 1969, to N. A. Crites

U.S. Pat. No. 4,265,243, issued May 5, 1981, to Glenn N. Taylor

U.S. Pat. No. 4,301,811, issued Nov. 24, 1981, to Terry N. Layton

U.S. Pat. No. 3,437,088, issued Apr. 8, 1969, to L. J. Bielinski

U.S. Pat. No. 4,214,593, issued July 29, 1980, to Imbruce et al

GENERAL DESCRIPTION OF THIS INVENTION

It is an aspect of this invention to provide an improved urodynamic catheter which can be utilized for carrying out all of the tests described above.

More particularly, this invention provides a urodynamic catheter which includes a tube of uniform section having at least four lumens and a closed leading end. A first one of the lumens communicates with a first side opening in the tube spaced a first distance from the leading end. A second lumen communicates with a second opening spaced a second distance from the leading end, the second distance being greater than the first distance. A third lumen communicates with a third side opening in the tube spaced a third distance from the leading end, the third distance being greater than the second distance. A fourth lumen communicates with the interior of an inflatable balloon attached to the tube and located between the second and third openings.

GENERAL DESCRIPTION OF THE DRAWINGS

Two embodiments of this invention are illustrated in the accompanying drawings, in which like numerals denote like parts throughout the several views, and in which.

DETAILED DESCRIPTION OF THE DRAWINGS

Figure 1:
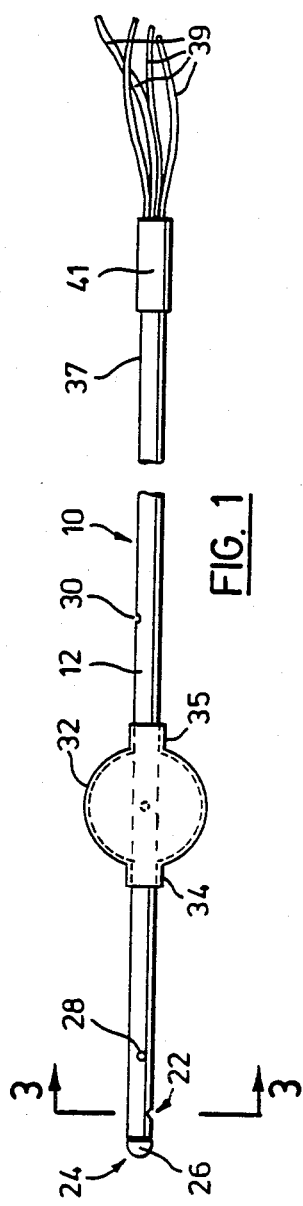
FIG. 1 is a partly broken away elevational view of a first embodiment of the urodynamic catheter of this invention.
Figure 3:
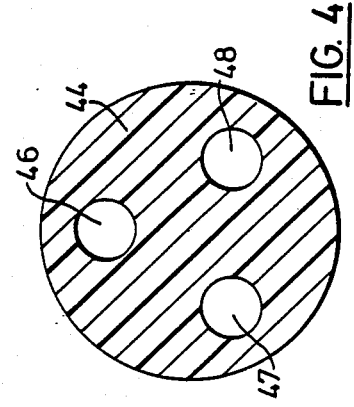
FIG. 3 is an enlarged sectional view taken at the line 3—3 in FIG. 1.

Attention is first directed to FIG. 1, which shows a catheter 10 which includes a tube 12 and four internal passageways or lumens 14, 15, 16 and 17, as can be seen in FIG. 3. One of the lumens, that numbered 16 in FIG. 3, communicates though a bore hole 20 with a first side opening 22 which is spaced back from the leading end 24 of the tube 12. The distance from the leading end 24 through the opening 22, in the embodiment illustrated, is approximately 7 mm. The opening 22 and the lumen 16 are intended to be used for bladder filling, and therefore the opening 22 should be located reasonably close to the leading end 24 of the catheter. The actual leading end 24 is capped by a closure member 26 which is heat sealed or otherwise affixed to the cut end of the tube 12, in order to close all lumens. As can be seen the closure end 26 is rounded, for ease of insertion. The closure member itself has a length of about 3 mm, leaving approximately 4 mm between the actual cut end of the tube and the location of the opening 22. It is to be understood that this particular distance could vary, but that it is of advantage to have the filling opening 22 located as close as possible to the leading end 24. A second one of the lumens, that numbered 15 in FIG. 3, communicates through a bore with a second side opening 28 in the tube 12. The purpose of the lumen 15 and the side opening 28 is to monitor the intravesical pressure as the bladder is being filled through the opening 22. This allows the cystometrogram to be plotted, this being a plot of intravesical pressure (pressure within the bladder) against volume of bladder contents. A third lumen, that numbered 14 in FIG. 3, communicates though a bore hole with a third side opening 30 which is spaced further back from the leading end 24.

The opening 30 is used to monitor closure pressure during cystometry. The location of the opening 30 will vary due to the different location of the urethral sphincter in male and female patients.

In addition, the side opening 30 and its associated lumen 14 are used to establish the urethral pressure profile (UPP), which determines compliance along the urethra wall. As previously described, a constant infeed of saline solution (0.9% NaCl) is applied through the opening where the UPP is being determined, and the back pressure is measured and plotted against longitudinal position along the urethra.

The last lumen, numbered 17 in FIG. 3 communicates through the bore with the interior of a balloon 32. The balloon is made of expandable material and is adapted to assume a substantial spherical shape when inflated. The balloon 32 includes two collars 34 and 35 through which the tube 12 passes, and which are heat sealed or otherwise affixed to the tube 12 in a liquid-tight manner. When deflated, the balloon 32 lies closely adjacent the tube 12, so as not to interfere with insertion or withdrawal of the catheter. When the balloon 32 is inflated, by providing pressurized liquid though the lumen 17, it prevents the catheter from falling out during the investigation, and also allows cystometric examination in the standing position or during certain exercises for detecting urinary incontinance (stress incontinance).

It will be understood that during the UPP test, the balloon 32 would be deflated and collapsed against the tube 12.

At the outer or non-insertion end of 37 of the tube 12, there is a connection with a plurality of smaller single-lumen tubes 39, which form the connections to the various pumps, gages, etc. which are used for the urodynamic tests described. The connection is normally made by supling a small coupling member in which are embedded four small-diameter hollow pins, each one being adapted to fit snugly within one of the lumens of the tube 12 at one end, and within the single lumen of one of the tubes 39 at the other end. Once these connections have been made, a sleeve 41 is fitted around the connector and heat sealed or otherwise fixed in place. The construction of this connecting location is conventional, and need not be described or illustrated in detail.

Although not illustrated in FIG. 1, the tube 12 has a plurality of markings at regular spacings along its length, particularly for use during the UPP test. Typically, these markings would be located at 1 cm intervals.

Figure 2:
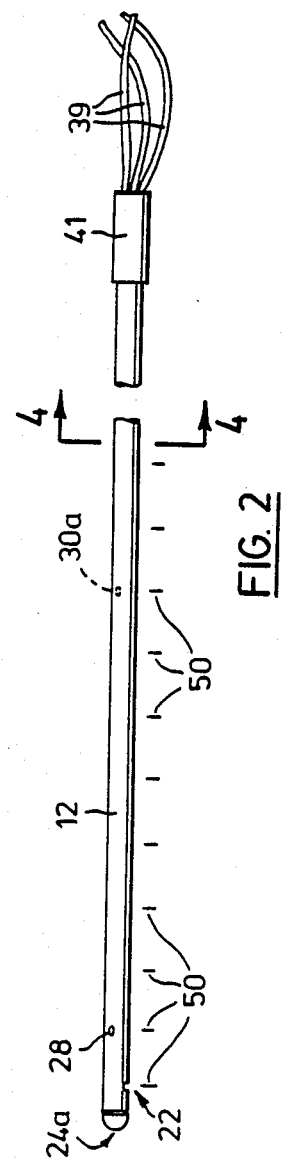
FIG. 2 is a partly broken away elevational view of a second embodiment thereof.

Attention is now directed to FIG. 2, which shows a modified form of the catheter of this invention, differing from that of FIG. 1 primarily in the absence of the balloon 32 and the absence of the side opening communicating with the interior of the balloon. Another difference relates to the location of the opening 30a, which in FIG. 2 is closer to the leading end 24 than is the opening 30 to the leading end 24 in FIG. 1. However, as previously mentioned, the location of the side openings 30 (30a) will vary depending upon the sex of the patient, and the preference of the end user.

The remaining openings in FIG. 2 are identified by the same numerals as in FIG. 1.

Figure 4:
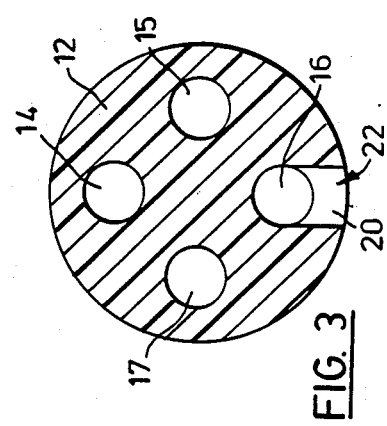
FIG. 4 is an enlarged sectional view taken at the line 4—4 in FIG. 2.

It will be understood that the tube 12 for the FIG. 2 embodiment would typically be a three lumen tube such as is shown at 44 in FIG. 4. The lumens are identified by the numerals 46, 47 and 48. However, there is no reason why a four-lumen tube could not be utilized for the FIG. 2 embodiment, with only three of the lumens active, and the other lumen being closed. It will be understood, in a general way, that a tube for use with this invention needs to have at least a number of lumens corresponding to the opening, (including the opening for the balloon if a balloon is present), but that additional lumens could be provided, and simply not utilized.

It will be evident from the foregoing description how the two embodiments of the catheter of this invention may be utilized for establishing the parameters described under the heading "Background of This Invention". It will further be understood that the lumen communicating with the opening 30 (30a) can be utilized to monitor closure pressure during cystometry.

In FIG. 2, a series of marker positions 50 have been drawn adjacent to the tube 12, to show the locations of longitudinally spaced marks used during the UPP test.

It is desirable to give an approximate idea of suitable or satisfactory dimensions for the spacings of the various openings, although these are not given with any intention to be limiting. In a satisfactory catheter constructed in accordance with FIG. 1, the opening 22 is located 7 mm away from the leading end 24, and the spacing between openings 22 and 28 is approximately 1 cm. Thus, the distance from the leading end 24 to the opening 28 is approximately triple the distance from the leading end 24 to the opening 22. From the opening 22 to the opening 30, a suitable distance is approximately 8 cm, with the balloon 32 being located somewhat closer to the opening 30 than to the opening 28.

For the catheter of FIG. 2, the opening 22 may again be located about 7 mm from the leading end 24a and the spacing between the openings 22 and 28 may be about 1 cm. The distance from the opening 22 to the opening 30a may be about 7 cm. Again, these distances may vary, particularly due to the fact that the position of the opening 30 (30a) depends somewhat on the sex of the patient and the preference of the individual examiner.

Each lumen may have a diameter in the range of about 0.8 mm, and the tube itself may have a diameter of around 3.3 mm.

While specific embodiments of this invention have been illustrated in the accompanying drawings and described in the foregoing disclosure, it will be apparent to those skilled in the art that changes and modifications may be made therein without departing from the essence of this invention as set forth in the appended claims.

I claim:

1. A urodynamic catheter for conducting urodynamic tests, comprising:

a tube of uniform diameter having at least four lumens and a closed leading end for intra-urethral insertion, a first one of said lumens communicating with a first side opening in the tube spaced a first distance from said leading end, a second one of said lumens communicating with a second side opening in the tube spaced a second distance from said leading end, said second distance being greater than said first distance, one of said first and second lumens being adapted to admit a liquid into the bladder, the other being adapted to monitor bladder pressure, a third one of said lumens communicating with a single third side opening in the tube, spaced a third distance from said leading end, said third distance being greater than said second distance, the third lumen being adapted to determine an urethral pressure profile (UPP), and a fourth one of said lumens communicating with the interior of an inflatable balloon attached to the tube, the balloon being located between said second and third openings and being adapted, when inflated, to retain the catheter in place with respect to the bladder.

2. The catheter claimed in claim 1, in which said second distance is about triple said first distance.

3. The catheter claimed in claim 1, in which said third distance is between about 4 and 5.5 times as great as said second distance.

4. The catheter claimed in claim 1, in which the ratio of said first, second and third distances is substantially 1:3:12.5.

5. The catheter claimed in claim 4, in which said first distance is substantially 0.7 cm.

6. The catheter claimed in claim 1, in which the ratio of said first, second and third distances is substantially 1:3:11.

7. The catheter claimed in claim 1, in which said balloon is centered at a location along the tube which lies closer to said third opening than to said second opening.

8. The catheter claimed in claim 1, in which said leading end is closed by a rounded closure member which seals all lumens.

9. The catheter claimed in claim 1, further including markings at regular intervals along said tube.

10. The catheter claimed in claim 1, further including markings at regular intervals of 1 cm along said tube.

* * * * *